United States Patent [19]

Imai et al.

[11] Patent Number: 4,633,884

[45] Date of Patent: Jan. 6, 1987

[54] PHYSIOLOGICAL SIGNALS PROCESSING SYSTEM

[75] Inventors: Hideki Imai; Minoru Sasaki, both of Yokohama, Japan

[73] Assignee: Kabushiki Kaisya Advance Kaihatsu Kenkyujo, Tokyo, Japan

[21] Appl. No.: 613,293

[22] Filed: May 23, 1984

[30] Foreign Application Priority Data

May 24, 1983 [JP] Japan .................................. 58-89953

[51] Int. Cl.$^4$ ............................................... A61B 5/04
[52] U.S. Cl. ..................................... 128/696; 364/415
[58] Field of Search ................. 364/415; 128/695-710

[56] References Cited

U.S. PATENT DOCUMENTS

| | | | |
|---|---|---|---|
| 3,869,601 | 3/1975 | Metcalf | 364/460 |
| 4,109,243 | 8/1978 | Day et al. | 128/710 |
| 4,216,780 | 8/1980 | Rubel et al. | 128/699 |
| 4,250,888 | 2/1981 | Grosskopf | 128/702 |
| 4,409,614 | 10/1983 | Eichler et al. | 358/76 |
| 4,417,306 | 11/1983 | Citron et al. | 364/415 |
| 4,449,536 | 5/1984 | Weaver | 128/696 |

OTHER PUBLICATIONS

Ruttiman et al. "Compression of ECG by Prediction or Interpolation and Entropy Encoding" *IEEE Trans. Biomed. Eng.*, vol. BME-26, No. 11, Nov. 1979, pp. 613–623.

Schmitt et al. "ECG Data Compression for the Emergency Setting" *J. Clin. Eng.*, Jan.–Mar. 1979, vol. 4, No. 1, pp. 49–53.

Ahmed et al. "Electrocardiographic Data Compression Via Orthogonal Transforms" *IEEE Trans. Biomed. Eng.*, vol. BME-22, No. 6, Nov. 1975, pp. 484–487.

Cox et al. "AZTEC, a Preprocessing Program for Real-Time ECG Rhythm Analysis" *IEEE Trans. Biomed. Eng.*, Apr. 1968, pp. 128–129.

*Primary Examiner*—William E. Kamm
*Assistant Examiner*—Mitchell J. Shein
*Attorney, Agent, or Firm*—Finnegan, Henderson, Farabow, Garrett & Dunner

[57] ABSTRACT

In a physiological signals processing system including (a) a A/D conversion means for converting physiological signals into digital signals and (b) a data compression means for reducing the number of data points sampled from said digital signals, the improvement which comprises: said data compression means being provided with a first sampling means for sampling a pair of combined peak points from said digital signals by applying the second order differential conversion to said digital signals, and a second sampling means for sampling level points by the level detection of said digital signals in the portion where adjacent peak points are not combined.

2 Claims, 36 Drawing Figures

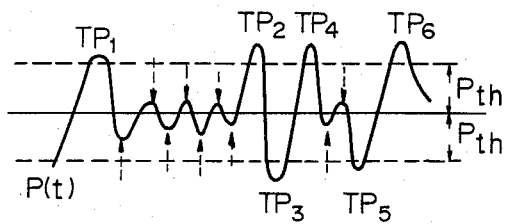
Fig.6(a)
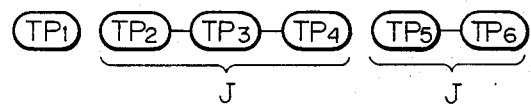
Fig.6(b)
Fig. 7
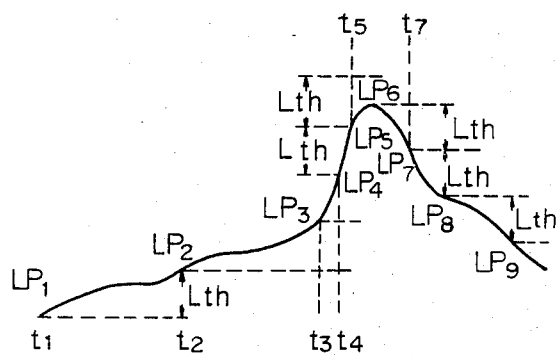

Fig.15(a)  Fig.15(b)  Fig.15(c)
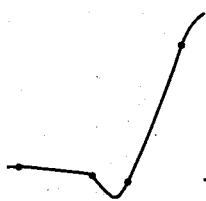
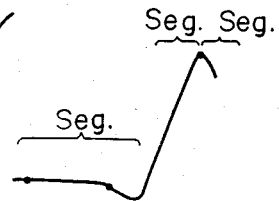
Fig.16(a)  Fig.16(b)

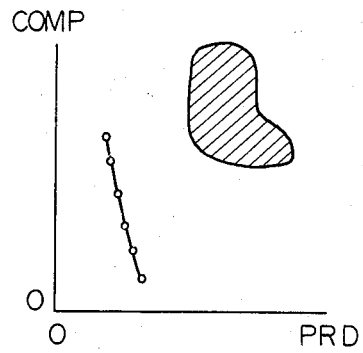
Fig. 32(A)
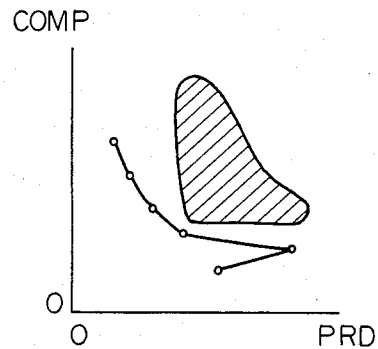
Fig. 32(B)
Fig. 33
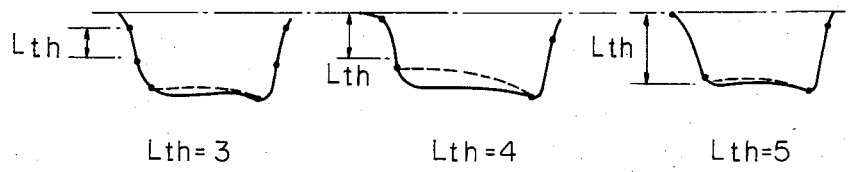
Lth=3  Lth=4  Lth=5
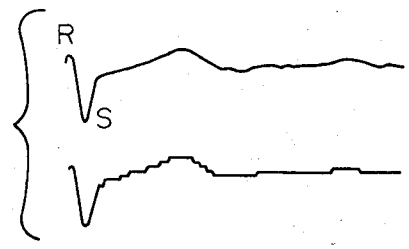
Fig. 34(a)
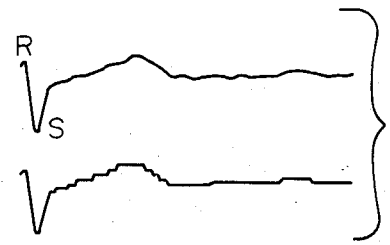
Fig. 34(b)

PHYSIOLOGICAL SIGNALS PROCESSING SYSTEM

BACKGROUND OF THE INVENTION

1. Field of the Invention

The present invention relates to a physiological signals processing system for compressing and reproducing physiological signals such as electrocardiogram signals and electroencephalogram signals.

2. Description of the Prior Art

When diagnostication is carried out by using an electrocardiographic waveform during a clinical examination, the pattern of the waveform is conventionally often recognized by a computer. This system is roughly divided into an on-line system and an off-line system according to the process by which electrocardiographic waveform is input to the computer. According to the on-line system, the waveform derived from the human body is directly input to the electronic computer. On the other hand, according to the off-line system, the waveform data is once stored in a memory medium and is then processed collectively.

In the electrocardiographic waveform, it sometimes happens that an abnormal wave of several heartbeats (cardiac arrhythmias) temporarily appears among the continuous normal waves. In order to detect such an abnormal wave, it is necessary to always monitor a patient. Most of the patients wherein abnormal waves temporarily appear are usually normal and live in the same manner as ordinary healthy people. The off-line system such as arrhythimia detection system for an ambulatory ECG monitor or Holter-type ECG is suitable for the examination of these patients. Namely, the electrocardiographic waveform is stored in a small device that can be attached to the human body and analysis is carried out afterward.

A large memory capacity is necessary for storing an electrocardiographic waveform recorded for a long time. Therefore, it is necessary to compress the waveform data. When the waveform data is compressed, it is indispensable that any error in the waveform reproduced from the original waveform should be small and, at least, the information necessary for correct diagnosis should be stored. Furthermore, according to the off-line system, it is necessary to process the waveform in real time by a processor having a small processing capacity, and hence, the algorithm should be simple and performed at a high speed.

The AZTEC (Amplitude-Time-Zone-Epoch-Coding) system is the most widely used data-reduction technique. However, it introduces significant discontinuities and distortion of the reconstructed signals.

SUMMARY OF THE INVENTION

The objects of the present invention are to eliminate the above-mentioned disadvantage of the prior art and to provide a physiological signals processing system for and accurately reconstructing the original signals such as electrocardiogram signals and electroencephalogram signals.

Other objects and advantages of the present invention will be apparent from the following description.

In accordance with the present invention, there is provided a physiological signals processing system including (a) a A/D conversion means for converting physiological signals into digital signals and (b) a data compression means for reducing the number of data points sampled from said digital signals, the improvement which comprises: said data compression means being provided with a first sampling means for sampling a pair of combined peak points from said digital signals by applying the second order differential conversion to said digital signals, and a second sampling means for sampling level points by the level detection of said digital signals in the portion where adjacent peak points are not combined.

BRIEF DESCRIPTION OF THE DRAWING

The present invention will be better understood from the description set forth below with reference to the accompanying drawings, wherein:

FIGS. 1 through 16 are diagrams illustrating the structure of the living body signal processing system of the present invention, in which FIG. 1 is a diagram showing an electrocardiographic waveform and characteristic points thereof, FIG. 2 is a diagram illustrating a linear estimate error, FIG. 3 is a frequency characteristic curve of a p-operator, FIG. 4 is a diagram illustrating a candidate of a peak point, FIG. 5 is a diagram illustrating a peak of a second difference point, FIGS. 6-(a) and 6-(b) are diagrams illustrating the state of combination of peak points FIG. 7 is a diagram illustrating sampling of characteristic points by the level conversion. FIG. 8 is a diagram illustrating a data compacting method, FIGS. 9 through 13 are diagrams illustrating interpolation using a spline function, FIG. 14 is a diagram illustrating slackening of a spline curve, FIGS. 15-(a), 15-(b) and 15-(c) are diagrams illustrating splitting into segments, and FIG. 16 is a diagram illustrating a boundary condition.

FIGS. 17 through 36 illustrate one embodiment of the present invention, in which FIGS. 17-(a) and 17-(b) are block diagrams showing the processing system of the present invention, FIG. 18 is a flow chart of the algorithm for sampling characteristic points, FIG. 20 is a flow chart of the algorithm for reconstruction, FIGS. 20-(1) through 20-(6) are diagrams showing examples of the electrocardiographic waveform, FIGS. 21 through 24 are diagrams comparing the compaction state in the processing system of the present invention with the compaction state in the AZTEC system, FIGS. 25 through 30 are diagrams illustrating approximate error PRD/compaction ratio COMP characteristics, FIGS. 31-(a) and 31-(b) are diagrams showing changes of threshold values of the PRD/COMP characteristics, FIG. 32 is a PRD/COMP characteristic curve according to Lth, FIG. 33 is a diagram showing changes of the error by Lth, FIG. 34 is a diagram showing changes of the AZTEC reconstructed waveform by Lth, FIG. 35 is a diagram illustrating the relationship between Lth and PRD, and FIGS. 36-(a) and 36-(b) are diagrams illustrating examples of the setting of threshold values by using Pth and Lth.

DESCRIPTION OF THE PREFERRED EMBODIMENT

The present invention provides a physiological signals processing system in which compression and reconstruction of the data points are carried out while taking the following two points (i) and (ii) into consideration.

(i) At the time of sampling the data points, informations important for determining the characteristics of the signals such as electrocardiographic waveform is sampled from the original signals as not having the significant distortion.

(ii) The reconstructed waveform can be composed of smooth curves.

According to the present invention, to satisfy requirement (i) or (ii), new data-reduction system for real-time data analysis is now provided as summarized above.

The structure of the present invention will now be described in detail.

Second Order Differential (Difference) Value

Figure 1:

It is considered that points indicating the characteristics of the electrocardiographic waveform are points where the inclination greatly changes, as shown in FIG. 1. In other word, points where the second order differential value greatly changes give a good indication of the characteristics of the waveform. There are various methods for giving a time differential value in a discrete signal, and the method using the difference as one operator is described below. The first order differential value or difference is expressed by the following formula:

$$v'(t) = v(t + nT/2) - v(t - nT/2) \quad (1)$$

(T: sampling period)

In the above formula, the signal is given by v(t) (t=1, 2, 3, ...).

The second order differential value or difference p(t) is then obtained from the formula (1):

$$p(t) = -v''(t) = v'(t - nT/2) - v'(t + nT/2) \quad (2)$$
$$= 2v(t) - v(t + nT) - v(t - nT)$$

Figure 2:
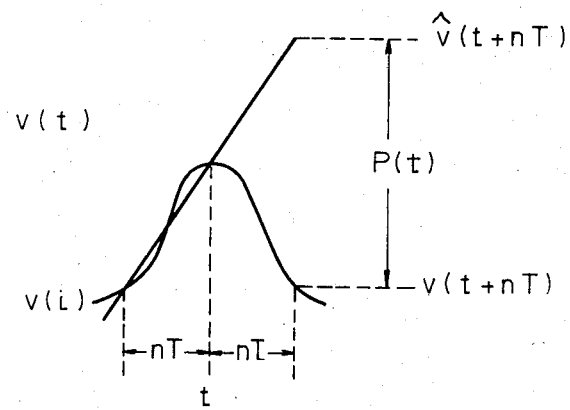

The operation according to formula (2) will be referred to as "p-operator" hereinafter. As shown in FIG. 2, the value of p(t) means a linear estimate error value. Namely, the wave height value v(t+nT) at the time t−nT is linearly estimated from v(t−nT) and v(t) as follows:

$$\hat{v}(t+nT) = 2v(t) - v(t-nT) \quad (3)$$

The difference between the estimate value $\hat{v}(t+nT)$ and the actual value v(t+nT) is p(t). Namely, the sampling by the p-operator is such that the waveform to be reconstructed is estimated and when the error of the estimated waveform from the original waveform exceeds a predetermined threshold value, this point is sampled. The formula (2) can be converted to the time region as follows:

$$P(\omega) = \int_{-\infty}^{\infty} 2v(t) \cdot e^{-j\omega t} dt - \int_{-\infty}^{\infty} v(t + nT) \cdot e^{-j\omega t} dt - \int_{-\infty}^{\infty} v(t - nT) \cdot e^{-j\omega t} dt \quad (4)$$

$$= V(\omega)(2 - e^{-j\omega nT} + e^{j\omega nT})$$

In the above formula, $V(\omega)$ is a value obtained by converting v(t) to the time region. Namely, $v(\omega)$ is expressed as follows:

$$V(\omega) = \int_{-\infty}^{\infty} v(t) \cdot e^{-j\omega t} dt \quad (5)$$

From formula (4), the p-operator is regarded as a filter having a frequency characteristic represented by the following formula:

$$P(\omega)/V(\omega) = 2(1 - \cos n\omega T) \quad (6)$$

Figure 3:
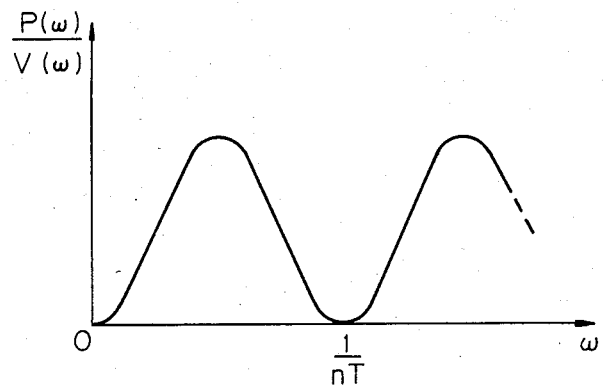

This filter has a characteristic as shown in FIG. 3. As is seen from the foregoing description, nT is an important parameter deciding the frequency characteristic of the p-operator.

Sampling by the Second Order Diffrential Conversion

Sampling by the second order differential conversion is accomplished by determining the peak of the second order differential (difference) value and sampling the corresponding point from the original waveform. In practice, however, many small peaks are caused to appear under the influence of noise and the like, and it is not easy to sample appropriate peaks. There has been proposed a method for smoothing the peaks, but this method is defective in that there is a risk of deviation in the peak positions. Accordingly, in the present invention, the peak of the second differential value is determined in the following manner.

First, t1 and t2 satisfying the requirements of the following formula are found:

$$p(t_1 - 1) \cdot p(t_1) < 0$$
$$p(t_2 + 1) \cdot p(t_2) < 0 \quad (7)$$

In the above formula, the plus or minus sign of p(t) is not changed in the range of from t=t1 to t=t2. Then, the maximum value of |p(t)| in the range of from t=t1 to t=t2 is found:

$$|p(tmax)| = \underset{t_1 \leq t \leq t_2}{\text{MAX}} (|p(t)|) \quad (8)$$

Figure 4:
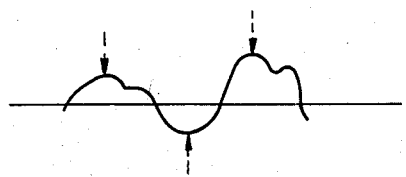

At this time, the point |tmax, p(tmax)| is treated as candidate of the peak point. Namely, as shown in FIG. 4, the maximum point |p(t)| in the wave group M of |p(t)| > 0 is a peak candidate which is indicated by a chain-line arrow. Among these peak candidates, one satisfying the requirement of the following formula is defined as a peak of the second order differential (difference) value:

$$|p(tmax)| \geq Pth \quad (9)$$

Figure 5:
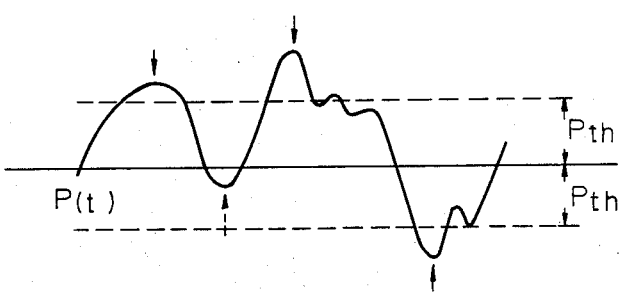

In the above formula, threshold Pth is an important parameter determining the characteristic of the sampling by the second order differential (difference) conversion. When a peak candidate meeting formula (9) is not present between t1 and t2, no peak is present in this section. All of these peaks are found and they are designated as Tp1, Tp2, ... in the sequential order. The foregoing procedures are collectively illustrated in FIG. 5, wherein peak candidates are indicated by a chain-line arrow and peaks are indicated by a solid-line arrow.

When there is no peak candidate between two adjacent peaks TPi and TPi+1, it is defined that the peaks TPi and TPi+1 are combined. Such a pair of peaks is also defiend as combined peaks. The two combined peaks indicate that sharp waves are concentrated in this portion. The reason is that the two peaks inevitably confront each other with the time axis being interposed therebetween and they correspond to acute maximum and minimum values in the original waveform. An example of the combined state of the peaks is shown in FIG. 6-(a) and the combined portion J is shown in the state diagram of FIG. 6-(b).

Sampling by Level Detection

Acute peaks such as those of QRS waves cannot be precisely sampled by the second order differential conversion as stated above. A portion such as an ST segment important for the diagnosis cannot be stably sampled and a large approximate error is produced on reconstruction. Therefore, another processing is carried out in a gentle portion and this processing is combined with the second order differential conversion to effect sampling over the entire region of the original waves.

The algorithm to be applied to the gentle portion will now be described. When processing is started at the time $t_0$, $t_i$ satisfying the requirement of the following formula is found:

$$W(t_0, t_1-1) \leq Lth \cdot \omega(t_0, t_1) > Lth \qquad (10)$$

In the above formula, $W(t_0, t_1-1)$ indicates a difference between the maximum and minimum values of the heart potential in the range from the time $t_0$ to the time $t_1-1$, and Lth is an important threshold value determining the characteristic of this algorithm. Then, the maximum point tmax, v(tmax) and minimum point tmin, v(tmin) between $t_0$ and $t_i$ are determined:

$$v(tmax) = \underset{t_0 \leq t \leq t_1}{MAX} (v(t)) \qquad (11)$$

$$v(tmin) = \underset{t_0 \leq t \leq t_1}{MIN} (v(t)) \qquad (12)$$

In case of tmax≠$t_0$, the maximum point is sampled and in the case of tmin≠$t_0$, the minimum point is sampled. Furthermore, in the case of tmax≠$t_0$≠tmin, the maximum point and minimum point are sampled.

Then, processing is started at the time t1, and points are similarly sampled. The processing is similarly repeated. The sampling by this algorithm will be referred to as "sampling by the level detection" or "level sampling" heareinafter. This algorithm is illustrated in FIG. 7. In FIG. 7, t2 meeting formula (10) is obtained by the processing started at t1. Namely, LP2 is sampled as the maximum point between t1 and t2, and similarly, maximum points LP3, LP4, and LP5 are sampled. At the processing between t5 and t7, the maximum point or minimum point does not overlap LP5, and therefore, the two points are simultaneously sampled. At the subsequent processing from t7, LP8 and LP9 are sampled as the minimum point.

Changeover of Mode

Sampling is carried out by effecting changeover between the two sampling methods described in the preceding paragraphs while checking the state of the waveform.

As described hereinbefore, in the portion where peaks of the second order differential values are combined, sharp waves are concentrated. Accordingly, the portion where peaks of the second order differential values are combined is regarded as the p-mode and only values sampled by the second differential conversion are regarded as being effective. The other portion is regarded as the level mode and sampling by the level detection is applied between the two peaks of the second order differential values that are not combined.

Figure 8:
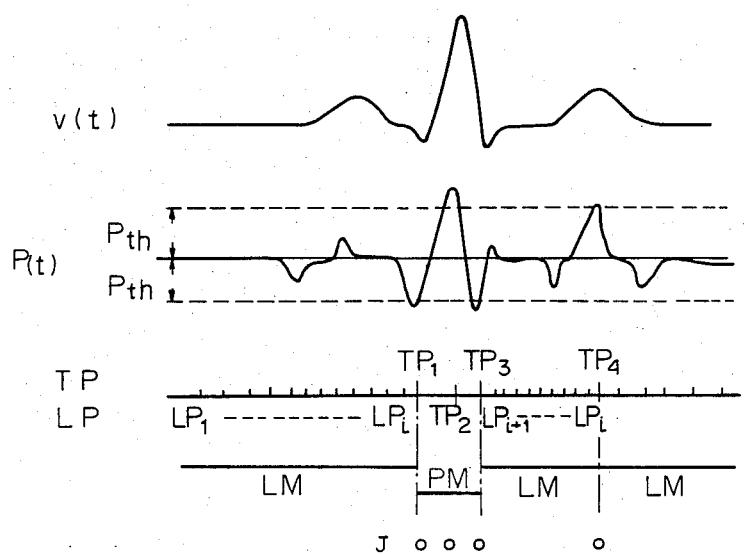

This feature will now be described in detail with reference to FIG. 8. In FIG. 8, v(t) stands for the original waveform, P(t) stands for the second order differential conversion (difference), TP stands for the point of sampling by the second order differential conversion (difference), LP stands for the point of sampling by the level detection, PM stands for the p-mode, LM stands for the level mode, and J indicates the state of combined peaks.

When processing is started at $t_0$, the first peak TP1 of the second difference value is sampled, and the level sampling is effected between $t_0$ and PT1 to sample LP1, LP2, ... LPi. Then, TP2 is sampled and it is confirmed that TP1 is combined with TP2, and the level sampling is not effected between TP1 and TP2. TP3 is then sampled, and it is confirmed that TP3 is not combined with TP2. When TP4 is sampled, since TP4 is not combined with TP3, the level sampling is effected in this section to sample LPi+1, ... LPj. As is apparent from the foregoing description, important characteristic points are sampled mainly by the second difference value, and in a relatively flat portion of the waveform, the level sampling is further effected. Whether or not the level sampling is effected is determined according to the combined state of peaks of the second difference value. The following three parameters determine the sampling characteristics.

n: This is represented by formula (6) and determines the frequency characteristic as the filter for the sampling by the second order differential value.

Pth: This is a threshold value represented by formula (9), which determines not only the characteristic by the sampling by the second order differential conversion but also the mode changeover characteristic. Namely, the smaller is Pth, the more combined are the peaks of the second difference value and the more dominant is the p-mode.

Lth: This is represented by formula (10) and determines the characteristic of the level detection sampling.

Spline Function

Figure 9A:
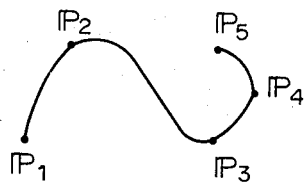
Figure 9B:
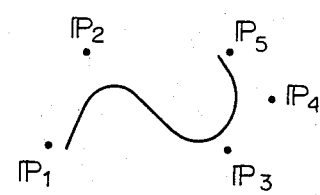

A spline function is usually adopted for forming a curve by interpolating points distributed in a space. There can be mentioned a method (interpolation) for forming a curve passing through the points as shown in FIG. 9-(a) and a method (approximation) for forming a curve not passing through the point as shown in FIG. 9-(b). In each case, the spline function is defined as the curve (t) minimizing Sk represented by the following formula:

$$Sk = \int_a^b \| q_{(t)}^{(k)} \| dt \; (k \leq n) \qquad (13)$$

In the above formula, $q_{(t)}^{(k)}$ is a k-th derivative of $q(t)$, and n is the number of points as reference. $q(t)$ is called a "k-th spline curve". Ordinarily, $q(t)$ is a $(2k-1)$-th order curve in the interpolation method and is a $(k-1)$-th order curve in the approximation method. Sk is a quantity indicating the smoothness, and an n-th order spline curve is most smooth. Ordinarily, a spline curve of k=2 is used. At this time, formula (13) is rewritten as follows:

$$S_2 = \int_a^b \|q''(t)\|^2 dt \quad (14)$$

This is interpreted as a curve minimizing the sum of changes of the gradient of the curve. The second spline curve by the interpolation method, that is, the third order spline curve, can be formed by solving a simple matrical equation.

Furthermore, a spline curve may be formed by combining Sk's differing in the order number. For example, in the case of k=1, formula (13) is rewritten as follows:

$$S_1 = \int_a^b \|q(t)\|^2 dt \quad (15)$$

Figure 10:
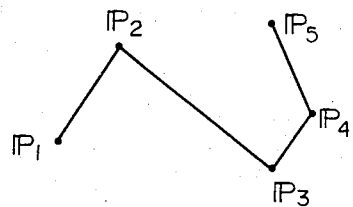

The spline curve is formed as a polygonal line as shown in FIG. 10. The formula (14) is coupled with formula (15) by a coefficient $\sigma$ as follows:

$$S_{12} = S_2 + \sigma^2 S_1 \quad (16)$$

The curve minimizing S12 has the characteristics of both formulae. This curve becomes a smoooth curve in the case of $\sigma \to 0$ and becomes a polygonal line in the case of $\sigma \to \infty$. This is called a spline under tension and $\sigma$ is called a tension factor. Also this curve is formed by solving a simple matrical equation.

Properties of Spline Curve

As described in the preceding paragraph, as the method for forming a spline curve, there can be mentioned the interpolation method and approximation method which are different in the manner of treating the reference points. The interpolation method suitable for reconstruction is adopted in the system of the present invention. In this paragraph, the properties of the spline curve formed by the interpolation method will be described. As the conditions for forming a spline curve, there can be mentioned (i) a boundary condition and (ii) a time condition.

(i) Boundary Condition

This is the condition for determining the state of both ends of one curve, and this condition is important when the formed curve is combined with another curve. The boundary condition is given by the following two methods.

(a) The curve is formed so that both ends become flection points. In this case, the curve has a shape to which no force is given from the outside.

(b) Inclination vectors are given to both ends. In this case, the formed curve has a shape such as if a force is applied from the outside.

Figure 11A:
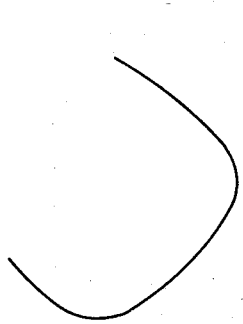
Figure 11B:
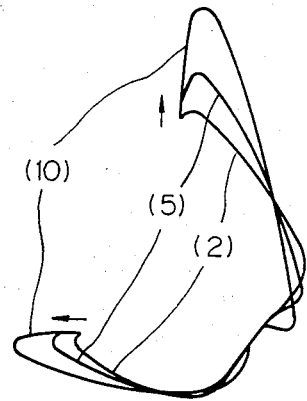

Examples of the boundary condition as shown in FIGS. 11-(a) and 11-(b). In the inclination vector-given curve shown in FIG. 11-(b), the direction of the vector is constant but the magnitude of the vector is changed. The arrow indicates the direction of the inclination vector given from the outside, and the parenthesized value indicates the relative magnitude of the inclination vector.

(ii) Time Condition

Figure 12:
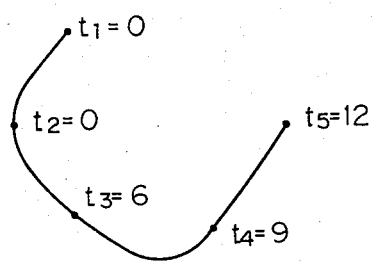

The formed curve (t) is expresed through the time t, and an optional time may be set for each interpolation point. In the curve of FIG. 11 formed under the natural condition, the times are equidistantly set as shown in FIG. 12. If $\tau i$ is defined as follows:

$$\tau i = t_{i+1} - t_i \quad (17)$$

all of $\tau$ in FIG. 12 are equal. Supposing that the length of the curve between the interpolation points is leni, the velocity Veli is defined as follows:

$$Veli = leni/\tau i \quad (18)$$

In the case of a spline curve, the curve is formed so that all of the velocities Veli are equal. Accordingly, in the portion where $\tau$ is relatively small, the curve approximates to a line, and in the portion where $\tau$ is relatively large, the curve is bulged. Furthermore, even if the values of $\tau$ are equal, in the portion where the distance between the interpolation points is greatly changed, the curve is bulged. This is phenomenon is called "slackening of the spline distance".

Figure 13A:
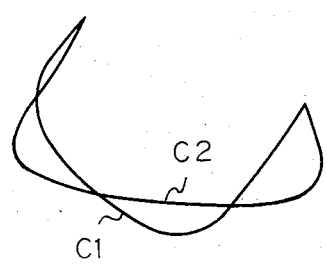
Figure 13B:
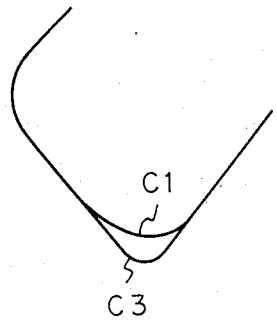

FIGS. 13-(a) and 13-(b) show changes of the spline distance caused when values of $\tau$ are partially changed as indicated below by C1, C2 and C3:

C1: $(\tau_1, \tau_2, \tau_3, \tau_4) = (3, 3, 3, 3)$

C2: $(\tau_1, \tau_2, \tau_3, \tau_4) = (3, 3, 1, 3)$

C3: $(\tau_1, \tau_2, \tau_3, \tau_4) = (3, 3, 9, 3)$

When $\tau i$ is partially changed as described above, a reverse action is exerted before and after this partial change.

Figure 14:

FIG. 14 shows an example in which the distance between the interpolation points is abruptly changed and slackening is caused in the portion indicated by an arrow. More specifically, if the portion where the distance between the interpolation points is short is adjacent to the portion where the distance between the points is long, slackening is caused in the portion where the distance between the interpolation points is short. Namely, it may be considered that this portion is influenced by the portion where the distance between the interpolation points is long.

Application of Spline Curve to Reconstruction of Electrocardiographic Waveform (1) Problem of Smoothness and Undulation The frequency distribution of the electrocardiographic waveform includes high frequencies of 100 to 200 Hz in the case of such peaks as those of R wave, and low frequencies of several Hz to scores of Hz are mingled in these high frequencies. Therefore, it cannot be said that the waveform is smooth. In other words, in order to form a waveform including many high-frequency components by a spline, it is necessary to perform interpolation by imparting many points to the other portion. However, the spline curve has a property such that in the portion where the distance between the interpolation points is abruptly changed, an undulation as shown in FIG. 14 is readily formed. It is difficult to predict such an undulation at the time of compaction. In this case, the undulation can be considerably diminished by using a spline-under-tension curve. In the system of the present invention, the spline-under-tension curve is used for reconstruction.

Futhermore, an undulation is caused before or after a sharp peak as in the cas of a QRS wave. Accordingly, the curve is split at this sharp point. Namely, characteristic points sampled from the original waveform V(t), indicated by dots in FIG. 15-(a), are not shown as one curve from the beginning to the end of the reconstructed waveform as shown in FIG. 15-(b), but different curves are formed for the respective segments Seg shown in FIG. 15-(c). If matching is effected without giving any condition on respective segments Seg, it often happens that an unnatural deformation is caused with the splitting point, indicated by the dot in FIG. 16-(a), being as the boundary. Accordingly, by imparting an inclination vector in the direction of the time axis as the boundary condition to both end points of each segment, matching is effected so that a continuous curve of a first order derivative is formed as the entire curve as shown in FIG. 16-(b).

The following formula is used for determining whether or not splitting into segments is performed on reconstruction:

$$\frac{V(ti) - V(ti+1)}{ti - ti+1} 1 \geq Sth \quad (19)$$

The i-th sampling point is expressed as Pi ti, V(ti). Sth is a threshold value for determining the condition for splitting into segments. Namely, if the inclination of the line connecting the point Pi to the point Pi+1 exceeds Sth, these two points become splitting points.

(2) Problem of Dimension

Since calculation is made on the interpolation points P and the corresponding elements of the curve C, an optional dimension may be adopted. If several spline curves shown in the preceding paragraph 3.2.5 are treated in the two-dimensional space, overlaps or loops are formed. Since an electrocardiographic waveform traces changes with the lapse of time, when a spline curve is applied, even if the curve is treated in the linear form, inherent properties can be retained. More specifically, the parameter t of the spline curve C(t) is made to correspond to the time of the electrocardiographic waveform. For example, when sampling points [t1, v(t1)], [t2, v(t2)], ... [t4, v(4)] are given, interpolation is effected on points v(t1), v(t2), ... v(t4), and the following time condition $\tau$ is given to each point:

$$(\tau_1, \tau_2, \tau_3) = (t_2-t_1, t_3-t_2, t_4-t_3) \quad (20)$$

Thus, the time between the sampling points can be set as $\tau$.

(3) Conditions for Formation of Curve

The conditions for formation of the reconstructed curve are fixed in the following manner according to the above-mentioned method.

(i) An inclination in the direction of the time axis is given to both end points of each segment as the boundary condition. (The time differential value of dC(t)/dt=0 is given.)

(ii) The time condition of $$\tau i = ti+1-ti \quad (21)$$

is set.

Parameters for determining the reconstruction characteristics, that is, the conditions for formation of the reconstructed curve, are as follows:

(1) Sth: This is a threshold value for determining the splitting that is represented by formula (17). The smaller this value, the larger the probability of splitting. A value is selected so that splitting is effected at peaks of the QRS wave.

(2) This is a tension factor in a spline-under-tension curve. In the case of $\sigma \to \infty$, the curve approximates to a polygonal line and in the case of $\sigma \to 0$, the curve becomes smooth.

Further the present invention includes the case using spline function and straight line approximation for reconstruction of ECG waveform. Spline function tends to yield distortion called "winding" at the area where the distance between each point abruptly changes. Though occurrence of the above distortion can be controlled by increasing the number of the sampled points to obtain the uniformity of the distance between each point, deterioration of the compressive rate is, in this case, unavoidable.

Accordingly, as methods for removing the distortion without increasing the sampled points, application of spline function under the tensile force as previously mentioned and that of partial straight line approximation are available. Application of straight line approximation is due to apprearance of areas of constant voltage level in cardiograms. Therefore, the straight line can interpolate the section where the voltage is constant through the successive sampled points.

Examples of The Present Invention

One embodiment of the present invention will now be described with reference to the accompanying drawings.

Figure 17A:
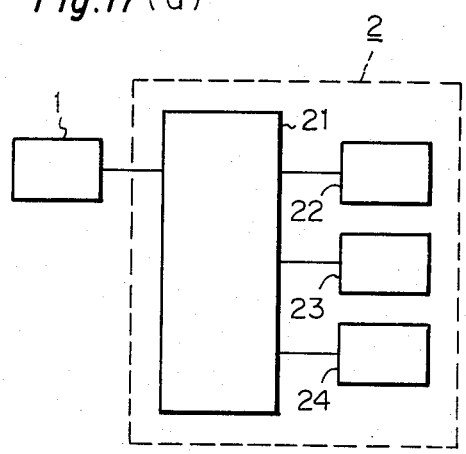
Figure 17B:
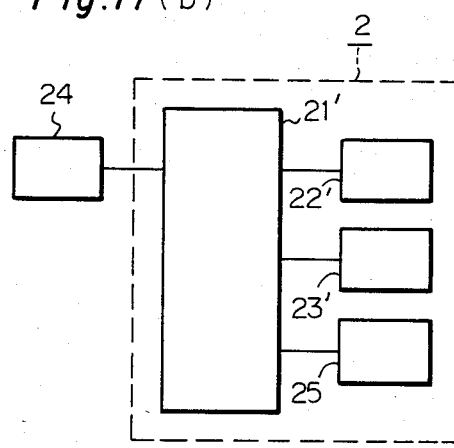

According to one embodiment of the physiological signals processing system of the present invention, a data computing zone comprises, as shown in FIG. 17-(a), A/D conversion means 1 for converting a living body signal derived from a living body, such as an electrocardigraphic signal, to a digital signal, and data processing means 2 including CPU (central processing unit) 21, a ROM (read-only memory) 22, a RAM (random access memory) 23 and a medium 24 for storing the data compacted.

The data processing means 2 functions with the CPU 21 as the central member, and the CPU 21 reads and executes instructions programmed in the ROM 22. The CPU 21 receives the living body signal digitalized by the A/D conversion means 1 and this signal is once stored in the RAM 23. Characteristic points of the original waveform of the living body signal are determined from the data stored in the RAM 23 according to the sampling algorithm described in the preceding paragraphs, and the compressed waveform is stored in the data storing medium 24.

Figure 18:
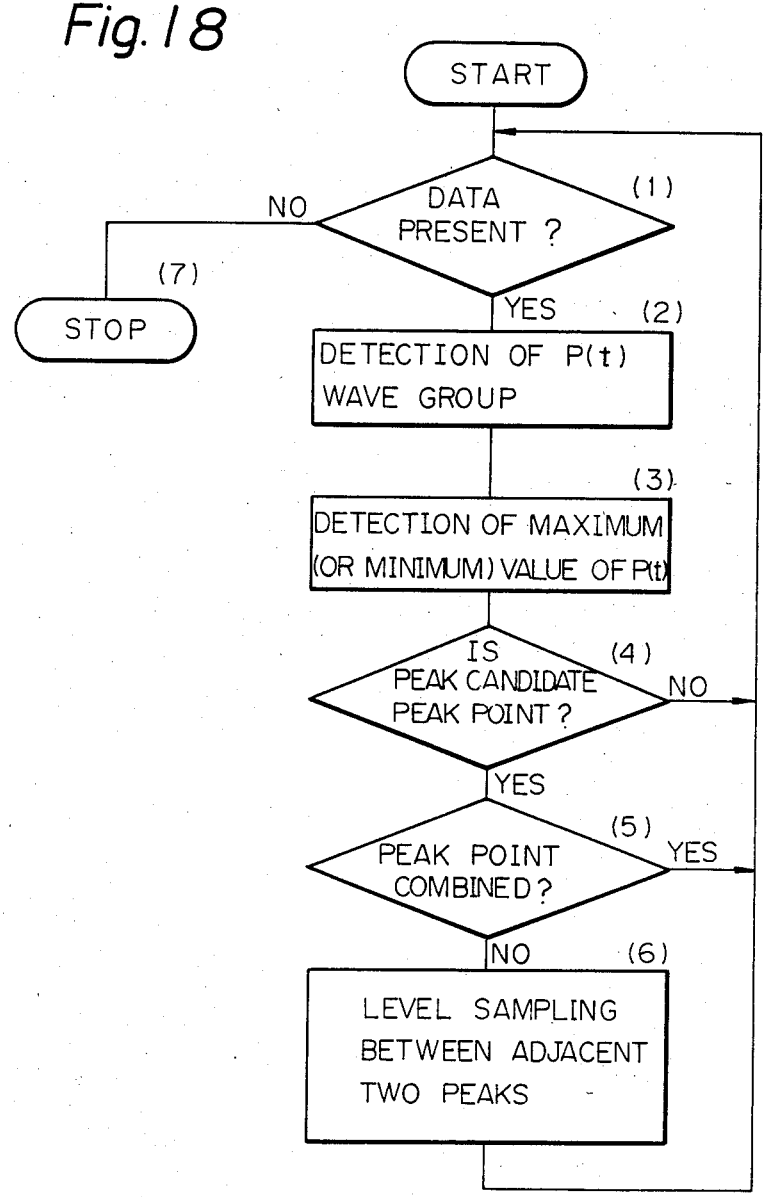

More specifically, the sampling algorithm in the data sampling means 2 comprises, as shown in the flow chart of FIG. 18, stage (1) of determining whether or not data to be processed is present, stage (2) of detecting the wave group of the second order differential value P(t) to the data to be processed, stage (3) of detecting the maximum and minimum values from the P(t) wave group, stage (4) of determining whether or not a peak point is a candidate of the peak point of the original waveform, stage (5) of determining whether or not the peak points judged as peak points among the candidates of peak points are combined, stage (6) of sampling a level point between two adjacent peak points by the level detection when it is determined that these adjacent peak points are not combined, and stage (7) of determining termination of processing when there is no data to be processed. When it is determined at the stage (5) that at least two peak points are combined, these peak points are regarded as characteristic points of the original waveform, and when it is determined at stage (5) that the adjacent peak points are not combined, the mode changeover of changing stage (5) to stage (6) is decided and the level points sampled at stage (6) are regarded as characteristic points of the original waveform. Thus, the data processing means effect reduction of the data by sampling the characteristic points according to the above-mentioned two modes. By this data compaction, a very large capacity of data can be stored in the data storing medium 24, and the original waveform can be reproduced without any significant error.

The data stored in the data storing medium 24 shown in FIG. 17-(a) is processed in the data processing means 2' having a similar structure to that shown in FIG. 17-(b) which constitutes a data reconstructing zone having a reconstructed waveform output portion 25.

The CPU 21' of the data processing means 2' receives the compressed data, and the compressed data is once stored in the RAM 23'. The reconstructed waveform of the original signals is formed from the data stored in the RAM 23' according to the reconstruction algorithm described in the preceding paragraphs and the reconstructed waveform is output from the reconstructed waveform output portion.

Figure 19:
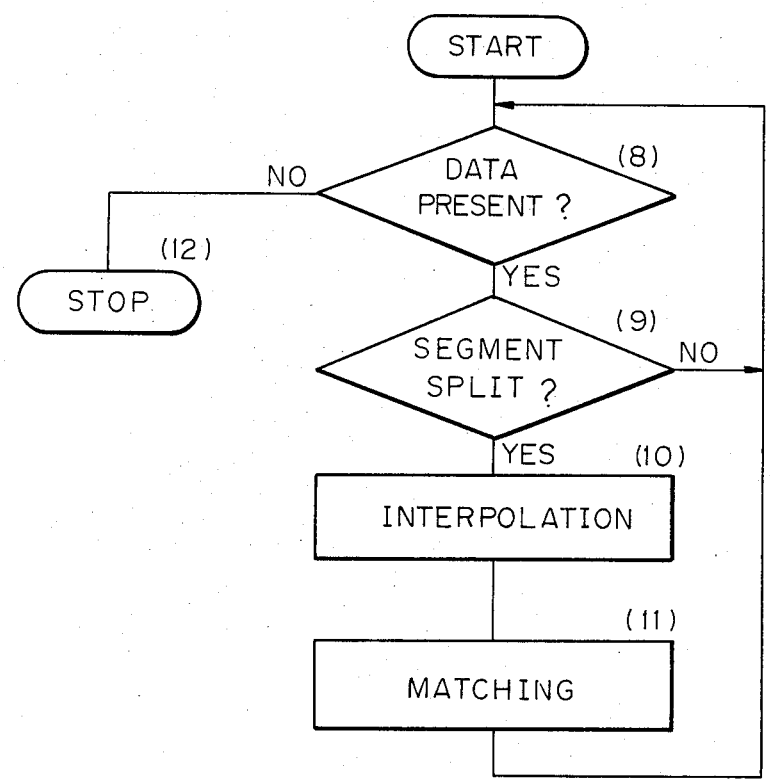

More specifically, the reconstruction algorithm in the data processing means 2' comprises, as shown in the flow chart of FIG. 19, stage (8) of determining whether or not there is data to be processed, stage (9) of determining whether or not the data to be processed should be split into segments, stage (10) of effecting interpolation on the characteristic points with respect to each segment by a spline curve, stage (11) of matching the interpolated segments, and stage (12) of determining termination of processing when there is no data to be processed. Every time matching of the segments is effected at stage (11), a reconstructed waveform appears at the reconstructed waveform output portion 25.

Comparison of Present Invention with Conventional Technique

The results of comparison of the physiological signal processing system of the present invention with of the conventional AZTEC system will now be described in detail.

Procedures

The digital electrocardiographic waveform used is one obtained by A/D conversion at a frequency of 500 Hz by 8 bits. Not only a standard waveform but also a waveform including an electromyogram is used as a sample. PRD (percent rms difference) represented by the following formula is used as an approximate error:

(i) rms Error: $rmse = \sum_{i=1}^{N} (v(i) - \bar{v}(i))^2/N$ (22)

(ii) rms Value: $ymsv = \sum_{i=1}^{N} (v(i))^2/N$ (iii) Percent Rms Difference: $PRD = \frac{rmse}{rmsv} \times 100$ v(i): original waveform $\bar{v}(i)$: reconstructed waveform The compaction ratio COMP is represented by the following formula:

$COMP = \frac{\text{number of sampled points}}{\text{number of samples of original waveform}} \times 100$ (23)

(present invention)

$COMP = \frac{\text{number of sampled plateaus and slopes}}{\text{number of samples of original waveforms}} \times 100$ (24)

(AZTEC)

Lth and Pth are changed in the processing system of the present invention and Lth and Pth are changed in the AZTEC system, and the results obtained are compared. The following values are used for the other parameters, unless otherwise indicated:

n = 10 (T = 2 × 10³ sec) (frequency characteristic of the point of second difference sampling)
Sth = 1.5 (dot/sample) (splitting)
σ = 0.3 (tension factor)

Results

Figure 20:
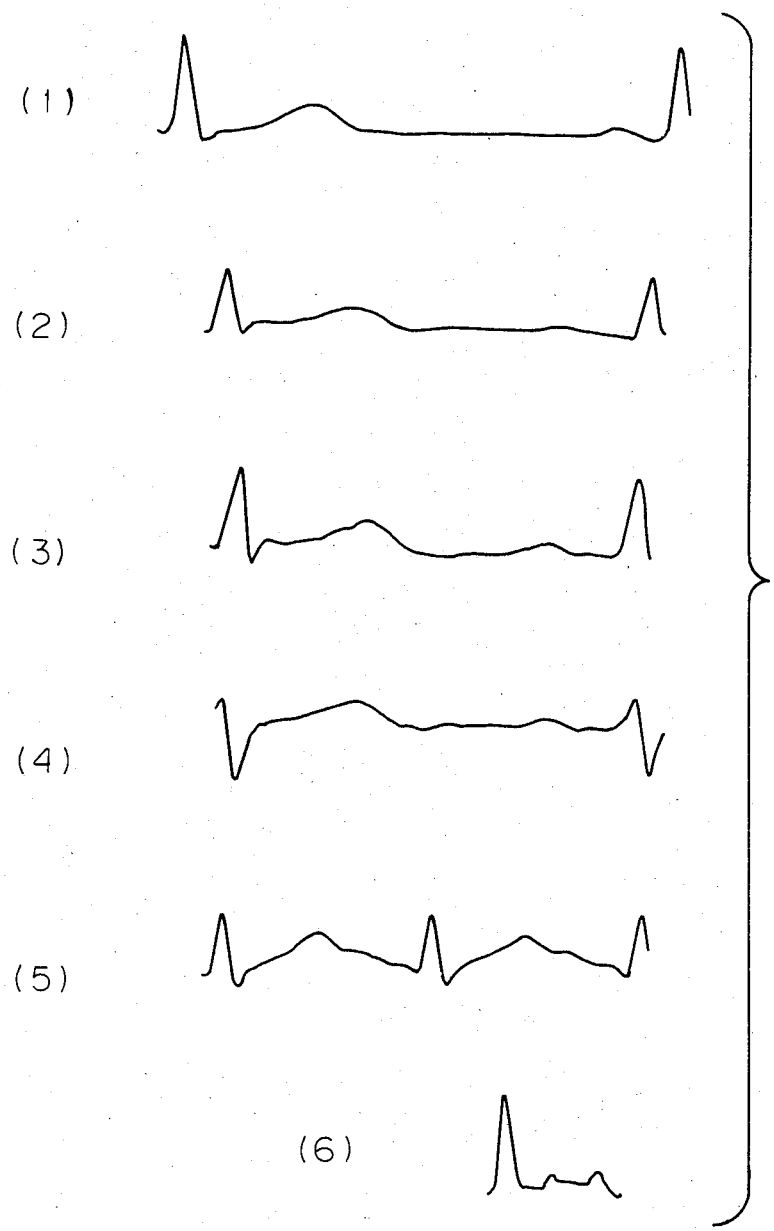

Electrocardiograms used for comparison of the processing system of the present invention with the AZTEC system are shown in FIGS. 20-(1) through 20-(6).

(i) Comparison of Compaction State

FIGS. 21 through 24 are time charts illustrating the compaction state in the processing system (a) of the present invention and (b) the compaction state in the AZTEC system.

With reference to the processing system (a) of the present invention, there are shown the original waveform V(t), the sampling point and splitting point P1 determined from the original waveform, the reconstructed waveform $\overline{V(t)}$, and the overlap V of the original waveform and reconstructed waveform.

With reference to the AZTEC system (b), there are shown the original waveform V(t), the boundary point P2 of the plateau or slope determined from the original waveform, and the reconstructed waveform $\overline{V(t)}$.

The results where the compaction ratios are substantially equal are selected from the results of both systems, and are shown together for facilitating comparison.

Figure 21A:
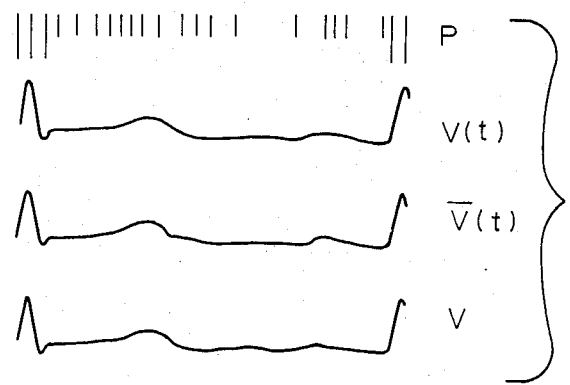
Figure 21B:
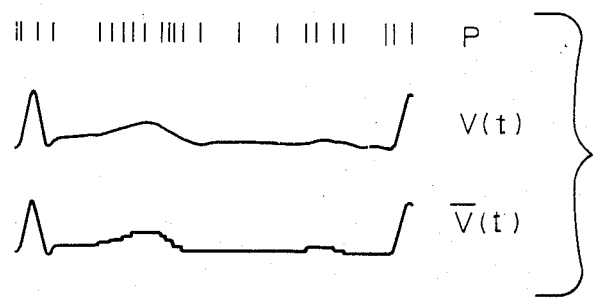

The electrocardiogram shown in FIG. 20-(2) is used for FIGS. 21-(a) and 21-(b). In FIG. 21-(a), the compaction ratio COMP is 6.0% and the approximate error PRD is 8.0%, and in FIG. 21-(b), the compaction ratio COMP is 5.9% and the approximate error PRD is 8.4%.

Figure 22A:
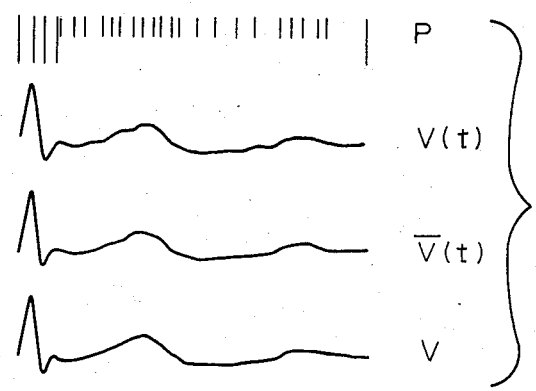
Figure 22B:
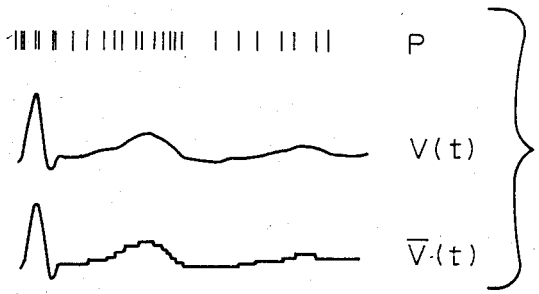

The electrocardiogram shown in FIG. 20-(3) is used for FIGS. 22-(a) and 22-(b). In FIG. 22-(a), COMP is 7.5% and PRD is 6.3%, and in FIG. 22-(b), COMP is 8.7% and PRD is 8.3%.

Figure 23A:
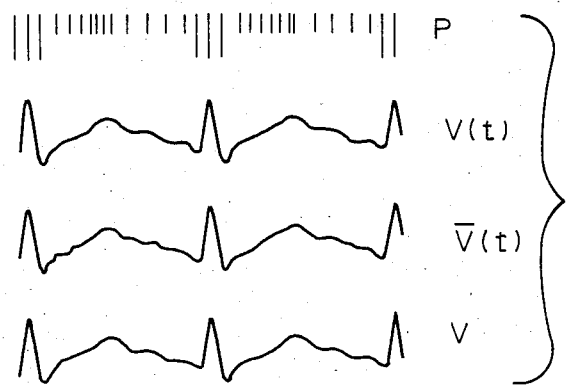
Figure 23B:
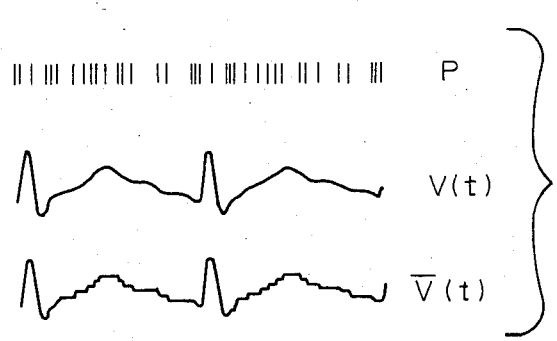

The electrocardiogram shown in FIG. 20-(5) is used for FIGS. 23-(a) and 23-(b). In FIG. 23-(a), COMP is 8.6% and PRD is 6.3%, and in FIG. 23-(b), COMP is 9.8% and PRD is 15.5%.

Figure 24A:
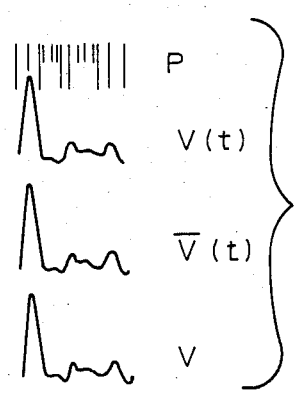
Figure 24B:
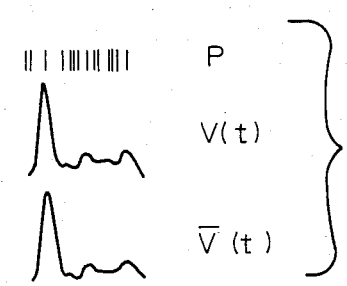
Figure 25:
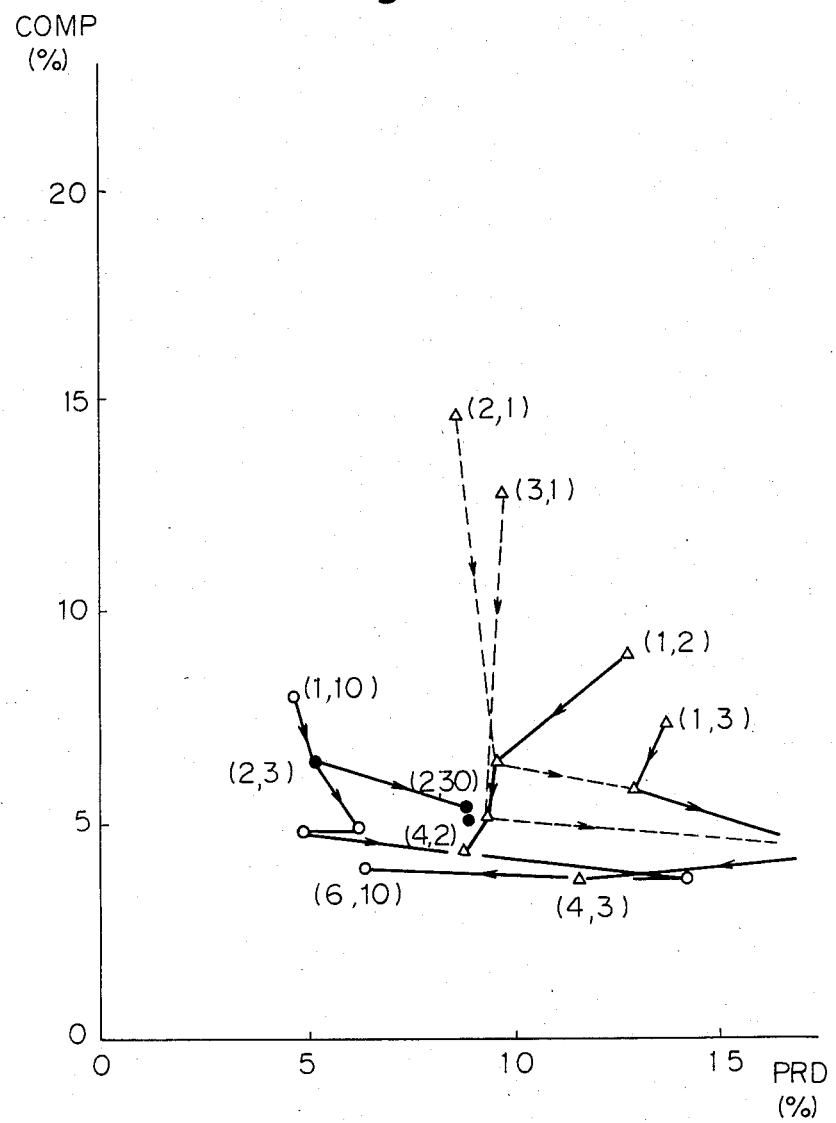
Figure 26:
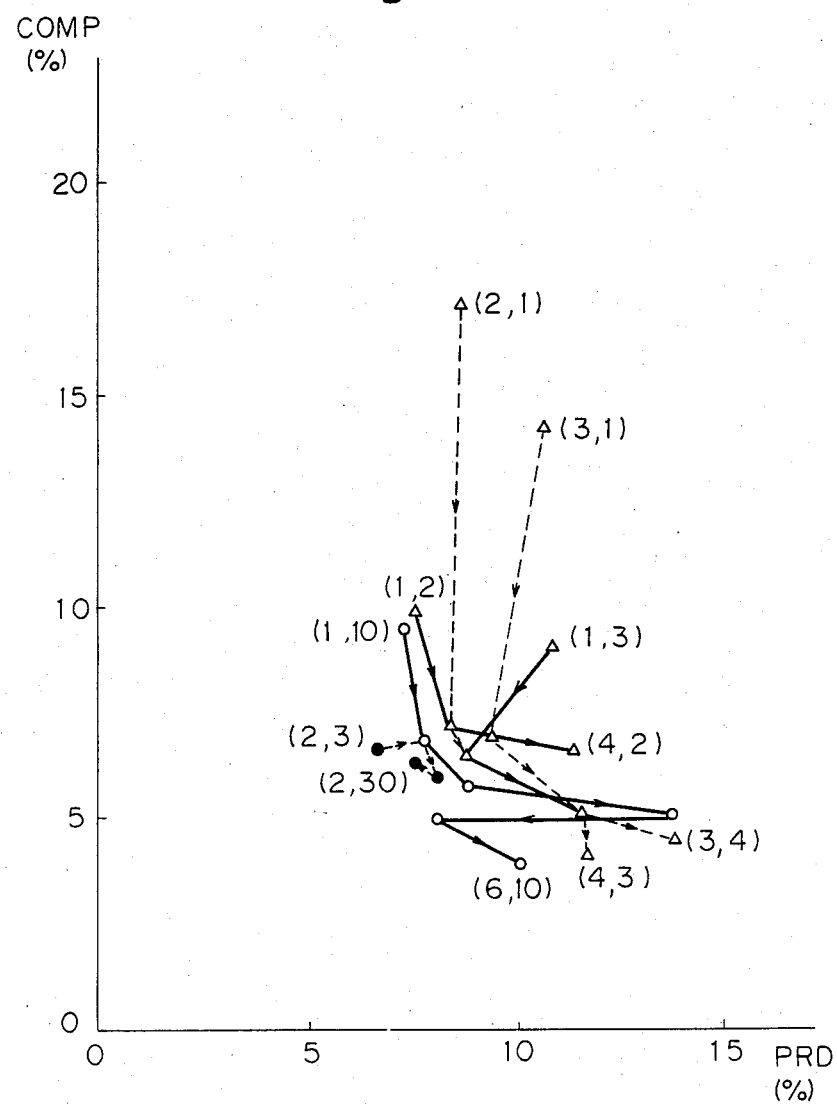
Figure 27:
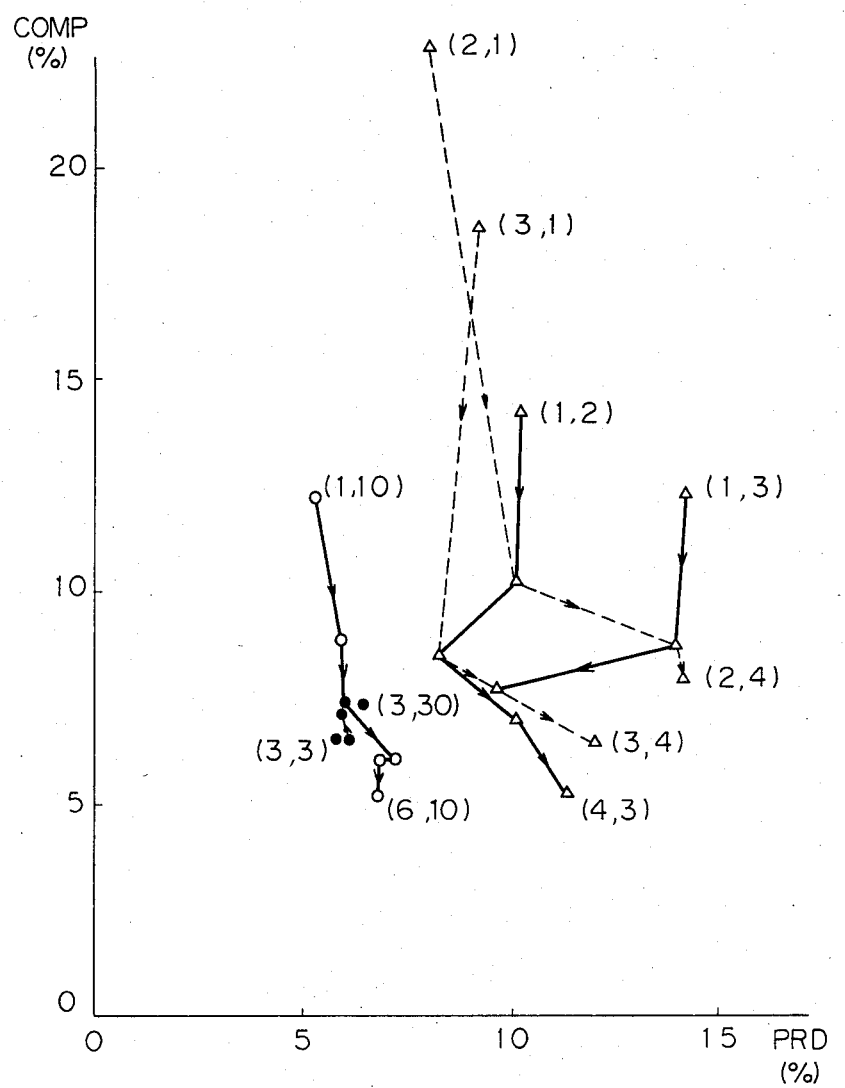
Figure 28:
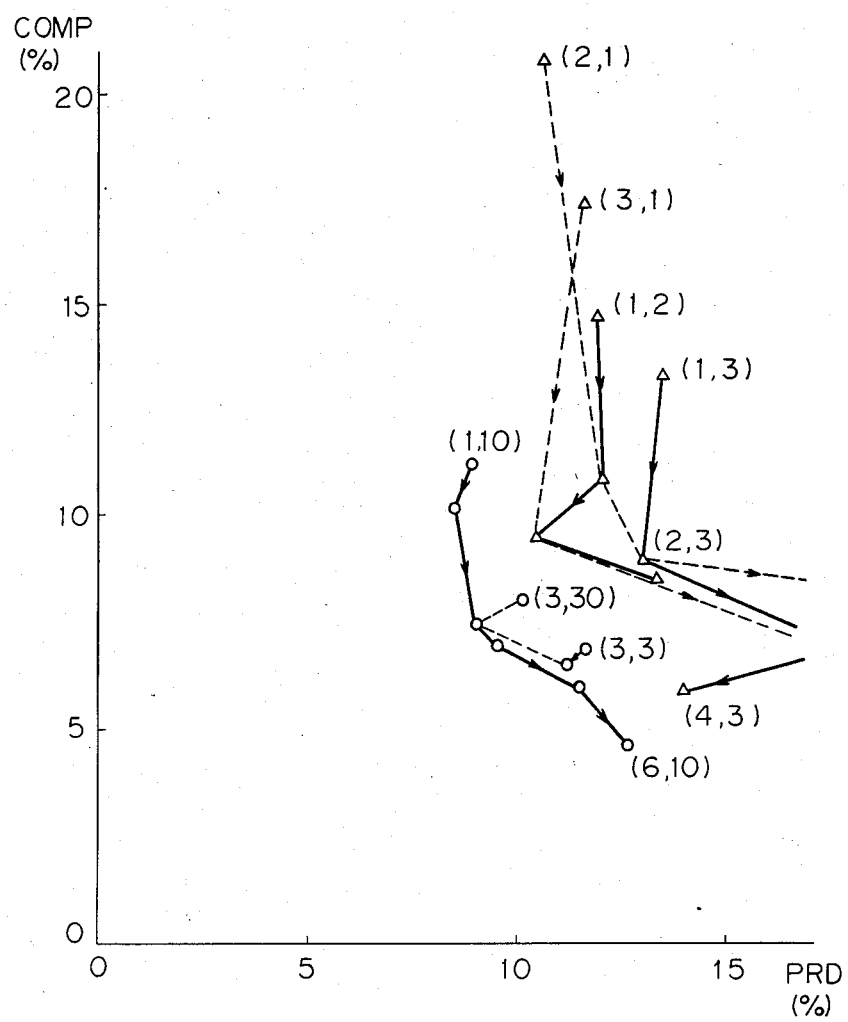
Figure 29:
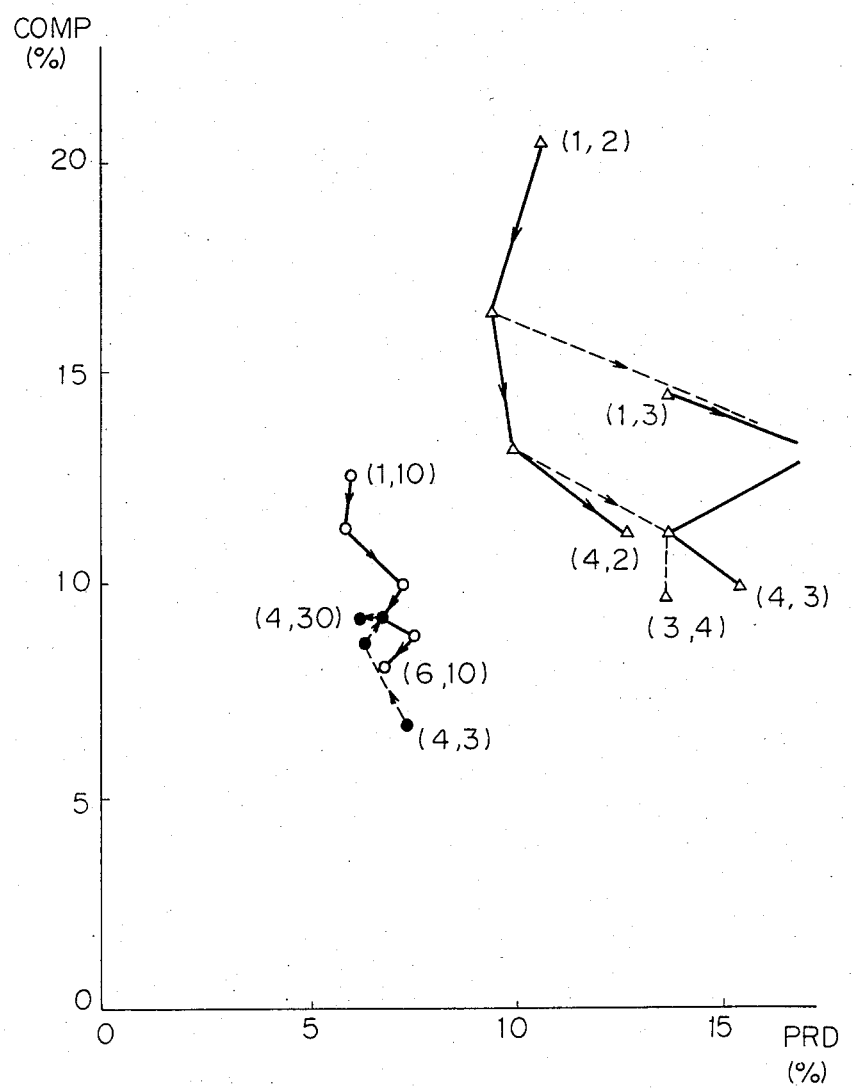
Figure 30:
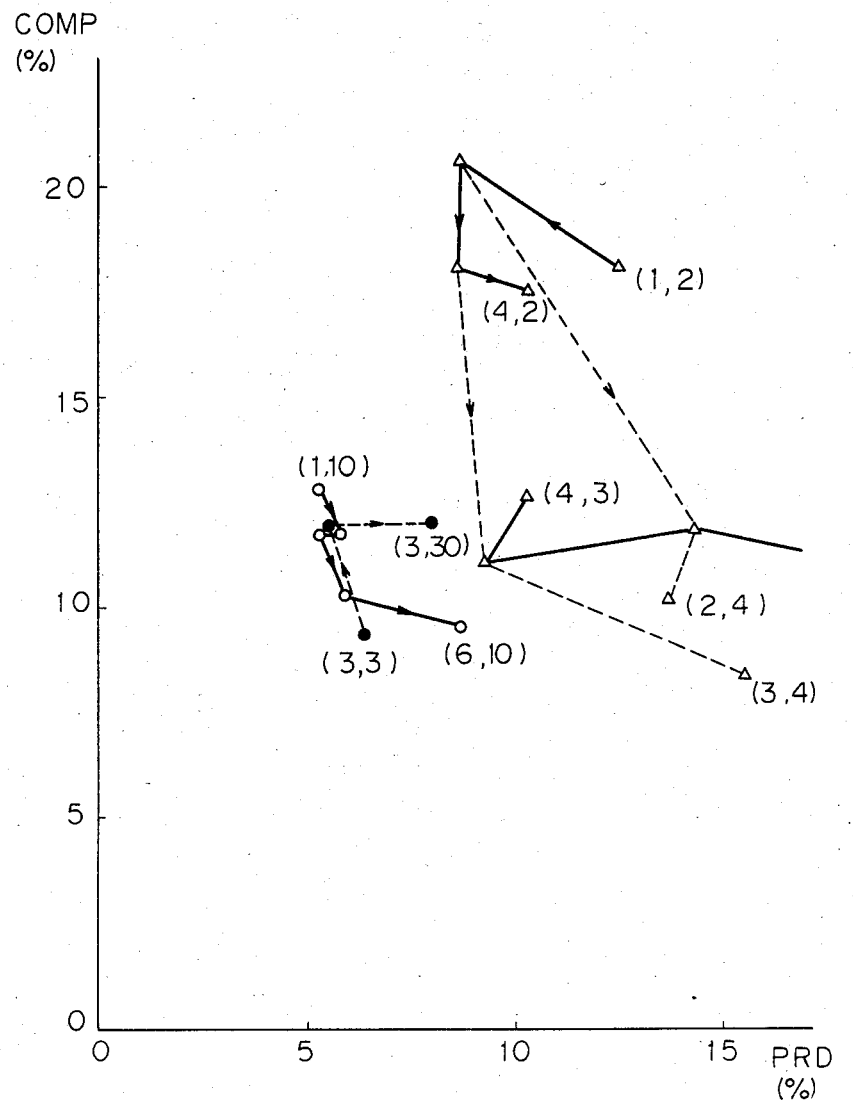

The electrocardiogram shown in FIG. 20-(6) is used for FIGS. 24-(a) and 24-(b). In FIG. 24-(a), COMP is 12.0% and PRD is 5.3%, and in FIG. 24-(b), COMP is 12.0% and PRD is 14%.

(ii) Compaction Ratio (COMP)/Approximate Error (PRD) Characteristic

Each of FIGS. 25 through 30 is a distribution diagram showing changes of the approximate error to the compaction ratio, observed when the threshold values Pth, Lth, and Tth are changed. In each diagram, black and white circle marks indicate the distribution obtained according to the processing system of the present invention, and triangular marks show the distribution obtained according to the AZTEC system. Furthermore, in each diagram, the parenthesized value indicates (Lth, Pth) or (Lth, Tth). Each distribution is connected through a chain line or solid line. The chain line and solid line indicate the characteristics obtained when one of the two threshold values is kept constant. The direction of the arrow is the direction along which the threshold value is increased.

The following electrocardiograms are used for FIGS. 25 through 30.
Electrocardiogram of FIG. 20-(1): for FIG. 25
Electrocardiogram of FIG. 20-(2): for FIG. 26
Electrocardiogram of FIG. 20-(3): for FIG. 27
Electrocardiogram of FIG. 20-(4): for FIG. 28
Electrocardiogram of FIG. 20-(5): for FIG. 29
Electrocardiogram of FIG. 20-(6): for FIG. 30

Figure 31A:
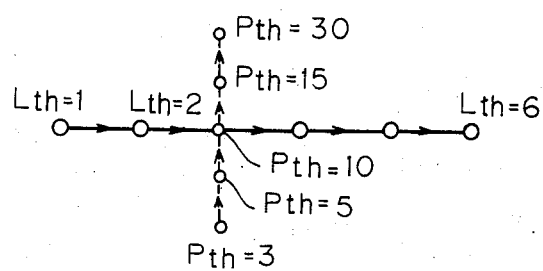
Figure 31B:
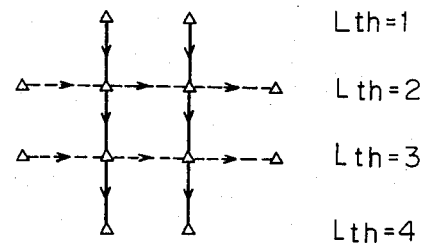

Changes of the threshold values of the PRD/COMP characteristic are shown in FIGS. 31-(a) and 31-(b). Note, FIG. 31-(a) shows the results obtained according to the processing system of the present invention, and FIG. 31-(b) shows the results obtained according to the AZTEC system. The unit of Lth is the dot, the unit of Pth is the dot, and the unit of Tth is the sample.

(iii) Tension Factor $\sigma$

The tension factor is a parameter for $\sigma$ reconstruction, and even if the tension factor is changed, the compaction ratio is not changed and even if the tension factor is greatly changed, the approximate error is not substantially changed. With reference to the electrocardiogram shown in FIG. 20-(3), the relationship between $\sigma$ and PRD is shown in Table 1. Note, Pth is 10.0 and Lth is 3.

TABLE 1

| s | 1.0 | 0.1 | 0.01 | 0.003 |
|---|-----|-----|------|-------|
| PRD | 6.8% | 6.2% | 6.4% | 6.4% |

Comparison and Consideration of Results

The characteristics of both systems will now be summarized from the results described in the preceding paragraph.

(1) General Tendency

From the PRD/COMP characteristics shown in FIGS. 25 through 30, it is seen that the compaction distribution according to the processing system of the present invention is present in the left lower portion as compared with the compaction distribution according to the AZTEC system, and this tendency is especially conspicuous when the waveform is sharp. This indicates that the processing system of the present invention is excellent over the AZTEC system in both the compaction ratio and the approximate error.

(2) Changes by Threshold Values

The threshold value Pth dominates the changes of the states of the modes. Namely, if Pth increases, the level sampling becomes dominant, and if Pth decreases, the sampling by the second difference value becomes dominant. In fact, if Pth is adjusted to 3.0 (the minimum value among the tested values), substantially all of the characteristic points are those sampled by the second difference value. When FIGS. 25 through 30 are examined, it is seen that if Pth is reduced, COMP becomes rather small. The reason is that the second difference value mode becomes dominant and the level sampling is hardly executed. Accordingly, in this case, PRD increases, though the increase is slight.

If the threshold value is changed, in each of the PRD-COMP characteristic curves obtained according to the processing system of the present invention and the AZTEC system, COMPT is ordinarily reduced with the increase of PRD. When examination is carried out more carefully, it is seen that the compaction according to the processing system of the present invention is divided into two types indicated by drawing lines through white circle marks in FIGS. 32-(A) and 32-(B). Note, the compaction according to the AZTEC system is included in the hatched region. In the type A shown in FIG. 32-(A), if PRD increases, COMP always tends to decrease, and this type A is obtained when entirely acute electrocardiograms as shown in FIGS. 20-(3) through 20-(6) are compacted.

In the type B shown in FIG. 32-(B), the PRD/COMP characteristic curve greatly fluctuates with the increase of Lth, and this type B is obtained when gentle electrocardiograms as shown in FIGS. 20-(1) and 20-(2) are compacted. In each of the electrocardiograms shown in FIGS. 20-(1) and 20-(2), the limit of the fluctuation of the characteristic curve resides in the point where Lth is 4. The reason is, that, as shown in FIG. 33, the sampling state in the vicinity of the plateau is changed by a slight change of the threshold value.

In the case of AZTEC, if the threshold value Tth is 1, the compaction ratio is drastically worsened. The reason is that, as shown in FIG. 34, most of portions to be inherently expressed as slopes are expressed as plateaus.

(3) Optimum Threshold Values

If certain threshold values are changed according to the waveform to be processed, the compaction ratio and approximate values can be minimized. For example, in the case of the electrocardiograms shown in FIGS. 20-(1) and 20-(2), if Lth is 3, both PRD and COMP are small, and this is an optimum value of Lth. If Lth is increased, the approximate error becomes large. On the other hand, in the case of the electrocardiograms shown in FIGS. 20-(3) and 20-(5), even if Lth is increased, the approximate error is not substantially changed, and an optimum value of Lth is larger than in the case of the electrocardiograms of FIGS. 20-(1) and 20-(2). Accordingly, optimum threshold values for ordinary waveforms will now be discussed in this paragraph.

As described in the preceding paragraph (2), even if the threshold value Pth is greatly changed, the approximate error and compaction ratio are not greatly changed. Accordingly, the following values are calculated and set for Pth used for simulation, and these values are summarized in Table 2:

| | |
|---|---|
| Pth = 100 × Pth/swing [%] | (25) |
| swing = maximum value of amplitude − minimum value of amplitude | (26) |

The threshold value Lth has a great influence on the approximate error and compaction ratio. However, Lth has an influence on a relatively flat portion to which the level sampling has been applied, and the state of this portion has no significant correlation to swing represented by the formula (26).

TABLE 2

| Setting Range of Pth (n = 10, T = 2 × 10³ sec) | | |
|---|---|---|
| Sample | Setting Range | Mainly Used Value |
| 1 | 3.3–30% | 11% |
| 2 | 3.3–30% | 10% |
| 3 | 5.3–53% | 18% |
| 4 | 3.5–35% | 12% |
| 5 | 4.7–47% | 15% |
| 6 | 3.2–32% | 10% |

TABLE 3

| | Values of ρ | | | | | |
|---|---|---|---|---|---|---|
| Sample | 1 | 2 | 3 | 4 | 5 | 6 |
| p | 4.7 | 4.3 | 6.4 | 5.1 | 7.1 | 5.0 |

The electrocardiogram of FIG. 20-(6) has a sharp waveform, but the value is small. The reason is that the level sampling has been applied only to a considerably flat portion [which does not appear in FIGS. 20-(1) through 20-(6) but is present before R wave[.

As the waveform is flat, Lth should be small. In contrast, it is considered that if the waveform is sharp, Lth can be increased. Accordingly, certain quantities indicating whether or not a waveform is flat should be determined.

Therefore, the following values of ri and ti are determined:

$$ri = \sum_{t=tib+nT}^{tie-nT} \{v(t+nT) - v(t-nT)\}^2 \quad (27)$$

$$ti = tie - tib - 2nT \quad (28)$$

In the above formulae, it is supposed that the i-th level sampling is effected in the range of from t=tib to t=tie. Namely, ri is obtained by squaring the differential value of v(t) and integrating the obtained value, and ti indicates the length of the integration section. The value of ρ is obtained from n of values of ri and n of values of ti according to the following formula:

$$\rho = \sum_{i=1}^{n} ri / \sum_{i=1}^{n} ti \quad (29)$$

This value indicates the state of the waveform in the portion to which the level sampling is applied. As the waveform is flat, ρ is small. Values ρ of the respective samples are shown in Table 3.

By using ρ, Lth is determined as follows:

$$Lth = Lth/\rho \quad (30)$$

Figure 35:
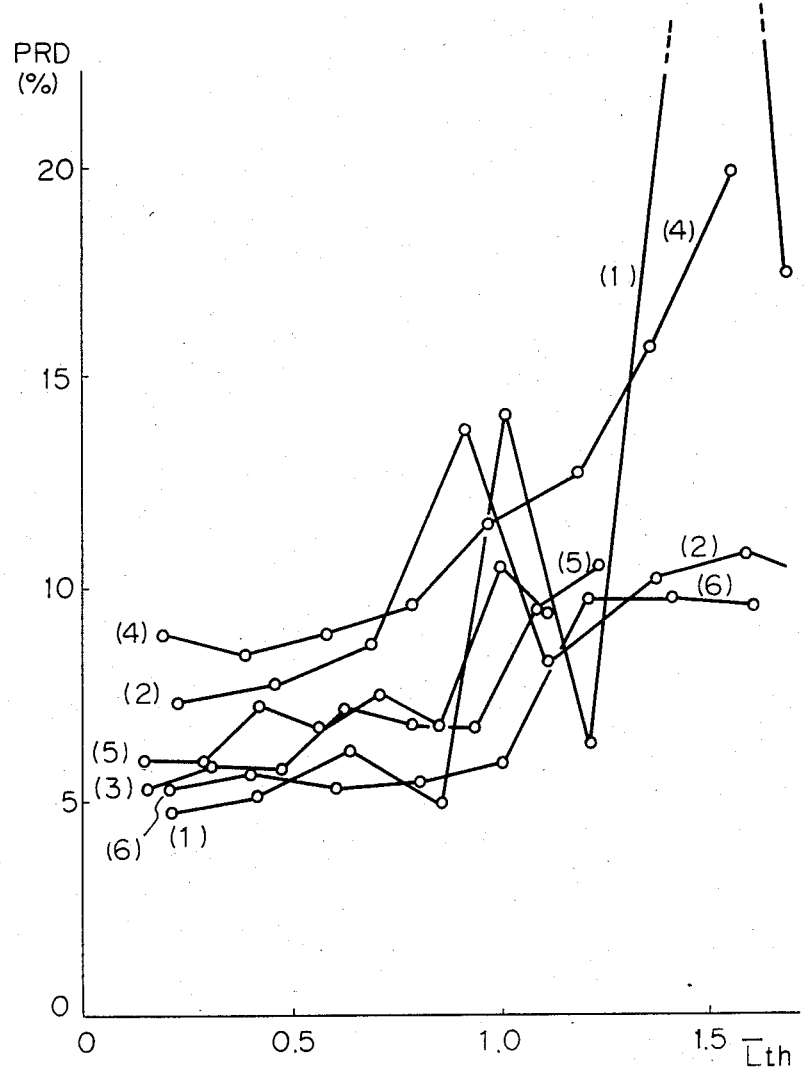

This Lth value is a threshold value determined while taking the state of the waveform into consideration. The relationship between PRD and Lth observed with respect to each of the samples of FIGS. 20-(1) to 20-(6) is illustrated in FIG. 35. From FIG. 35, it is seen that as Lth becomes large, the value of PRD ordinarily becomes unstable. Usually, it is in the case of Lth ≧0.6 that PRD becomes unstable, and this tendency is commonly observed in all waveforms. Accordingly, the upper limit is set at Lth=0.5 with a margin, and a threshold value can be preliminarily set for an unknown waveform by using this value. For example, in the case of the electrocardiograms of FIGS. 20-(3) and 20-(5), an optimum value of Lth=3 is set, and in the case of the electrocardiograms of FIGS. 20-(1), 20-(2), 20-(4) and 20-(6), an optimum value of Lth=2 is set.

Method for Setting Optimum Threshold Values in Processing System of Present Invention The method for setting optimum threshold values for unknown waveforms based on the matters described in the preceding paragraph will now be described.

(i) Pth 10 to 15% of swing defined by the formula (26) is set as the optimum value of Pth. If data of one preceding heartbeat is available, swing can be easily determined.

(ii) Lth

When the level sampling is effected, the waveform of the portion to which the level sampling is applied is examined and ρ is determined. Lth is calculated from a given value of Lth and the sampling is carried out by using the calculated value of Lth. At this time, Lth is changed according to the portion where the level sampling is effected.

In order to increase the reliability of setting methods (i) and (ii) and the values of Pth and Lth, simulation should be carried out on many other samples. However, it is considered that the methods (i) and (ii) provide certain criteria even at present.

Figure 36A:
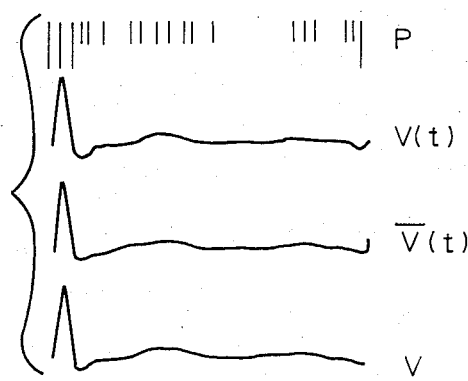
Figure 36B:
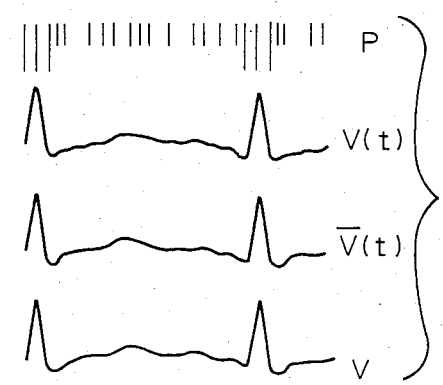

FIGS. 36-(a) and 36-(b) show the results obtained when threshold values are determined for unknown waves by using Pth and Lth and compaction is executed by using these threshold values. The data used includes Pth of 12% and Lth of 0.7 at 12 bits.

Other Parameters

When the processing system of the present invention is compared with the AZTEC system, other parameters Sth and n are fixed. As described in the preceding paragraph, even if these parameters are changed, the obtained results are not substantially changed. Sth is selected so that splitting is effected substantially as peaks of the QRS wave. If the value of n is too large, the sampling point is greatly deviated from the peak, and if the value of n is too small, infuences of the noise component become conspicuous.

Herein, the value of n=10, that is, nT=20 msec, is used as the empirically found value, and this corresponds to the time interval of the peaks of the QR wave. It has been reported that QRS wave groups are detected by the second difference value by utilizing the above-mentioned value.

These parameters can be fixed if the sampling frequency and A/D conversion bit number are determined.

As is apparent from the foregoing description, according to the present invention, by effecting A/D conversion of a physiological signals and sampling by the second order differencetial conversion, sharp peak points such as those of the QRS wave are sampled as characteristic points of the original waves, and by sampling by the level detection, level points of gentle portions such as ST segments are sampled as characteristic points of the original waves. Accordingly, the data can be efficiently compressed while the characteristic points of the original waveform of the signals are precisely grasped. Moreover, since interpolation is effected on the characteristic points of the data obtained by compressing the original waveform by applying spline function, a reconstructed waveform with no substantial distortion can be obtained.

We claim:

1. In a physiological signals processing system including (a) a A/D conversion means for converting physiological signals into digital signals and (b) a data compression means for reducing the number of data points sampled from said digital signals, the improvement which comprises: said data compression means being provided with a first sampling means for sampling a pair of combined peak points from said digital signals by applying a second order differential conversion to said digital signals, and a second sampling means for sampling level points by the level detection of said digital signals in the portion where adjacent peak points are not combined.

2. The system of claim 1 in which said system is further provided with a data reconstruction means for reconstructing signals by interpolating the sampled data points with a spline function modified by a tension factor so as to eliminate the distortion from the reconstructed signals.

* * * * *